(12) United States Patent
Hong et al.

(10) Patent No.: US 7,939,588 B2
(45) Date of Patent: May 10, 2011

(54) SALT OF CARBOXYETHYL PHOSPHINATE ESTER AND FLAME RETARDANT THERMOPLASTIC RESIN COMPOSITION CONTAINING THE SAME

(75) Inventors: Sang Hyun Hong, Uiwang-si (KR); Jeong Hwan Ku, Gunpo-si (KR); Su Hak Bae, Seoul (KR); Jin Hwan Choi, Anyang-si (KR); Jin Hwan Kim, Seoul (KR); Min Soo Lee, Ansan-si (KR)

(73) Assignee: Cheil Industries Inc, Gyeongsangbuk-do (KR)

( * ) Notice: Subject to any disclaimer, the term of this patent is extended or adjusted under 35 U.S.C. 154(b) by 833 days.

(21) Appl. No.: 11/563,648

(22) Filed: Nov. 27, 2006

(65) Prior Publication Data

US 2007/0155872 A1 Jul. 5, 2007

(30) Foreign Application Priority Data

Dec. 30, 2005 (KR) .................. 10-2005-0134991

(51) Int. Cl.
*C07F 5/06* (2006.01)
*C07F 9/02* (2006.01)
*C08K 3/32* (2006.01)
*C08K 5/49* (2006.01)
*C08L 31/00* (2006.01)

(52) U.S. Cl. .......... 524/115; 556/170; 556/174; 558/70; 562/876; 568/8; 524/556; 524/414

(58) Field of Classification Search ............. 556/174; 558/70; 56/876; 568/8; 562/876; 524/414, 524/556, 115
See application file for complete search history.

(56) References Cited

U.S. PATENT DOCUMENTS

| 5,089,559 A * | 2/1992 | Blount ............. 525/107 |
| 5,952,406 A | 9/1999 | Asrar |
| 6,613,822 B1 | 9/2003 | Eckel et al. |

FOREIGN PATENT DOCUMENTS

| JP | 62297323 A | * | 12/1987 |
| JP | 2008 013877 | | 2/1996 |
| KR | 1020020007813 | | 9/2000 |
| KR | 1020020094307 A | | 12/2002 |
| WO | WO 03089513 A1 | * | 10/2003 |

OTHER PUBLICATIONS

English Translation of JP 62297323 A, Dec. 1987, Usui et al.*

* cited by examiner

*Primary Examiner* — Vasu Jagannathan
*Assistant Examiner* — Karuna P Reddy
(74) *Attorney, Agent, or Firm* — Law Offices of John A. Parrish (57) ABSTRACT

A composition includes a salt of a carboxyethyl phosphinate ester compound. Additionally, the composition may also include a polymeric resin, such as a thermoplastic resin. The composition may have improved physical and chemical properties including flame retardancy, thermal stability, and hygroscopicity.

19 Claims, 3 Drawing Sheets

SALT OF CARBOXYETHYL PHOSPHINATE ESTER AND FLAME RETARDANT THERMOPLASTIC RESIN COMPOSITION CONTAINING THE SAME

CROSS-REFERENCE TO RELATED APPLICATIONS

This non-provisional application claims priority under U.S.C. §119(a) from Korean Patent Application No. 2005-134991 filed on Dec. 30, 2005, which is herein incorporated in its entirety by reference.

BACKGROUND OF THE INVENTION

1. Field of the Invention

The present invention relates to a composition comprising a salt of a carboxyethyl phosphinate ester. It additionally relates to flame retardant thermoplastic resin compositions comprising the same.

2. Description of the Related Art

In general, thermoplastic resins are used in almost all electronic products, owing to its good processability and mechanical properties. However, the thermoplastic resin by itself has little to no flame retardancy. One method of increasing flame retardancy of thermoplastic resins is the inclusion of a halogenated compound and antimony oxide. However, this method is not favorable because of the inclusion of halogen containing compounds which have a detrimental effect to the environment, including human health. As such, there is a present need for the design of thermoplastic resins which contain other flame retardant compounds which are safer to the environment and for human use.

SUMMARY OF THE INVENTION

Described herein are compositions comprising carboxyethyl phosphinate esters. In some particular embodiments, the composition comprise the salt of a carboxyethyl phosphinate ester. In particular embodiments, a composition comprises a compound represented by Formula (I):

In the formula, $R^1$ is independently selected from the group consisting of $C_1$-$C_6$ alkyl, $C_6$-$C_{20}$ aryl group and alkyl-substituted $C_6$-$C_{20}$ aryl, $R^2$ is independently selected from the group consisting of $C_1$-$C_6$ alkyl, $C_6$-$C_{30}$ aryl, and alkyl-substituted $C_6$-$C_{30}$ aryl group, n is 1, 2, 3 or 4, and M is a metallic ion or a charged amine.

In some particular embodiments, the amine is selected from the group consisting of ammonium, primary ammonium, secondary ammonium, tertiary ammonium, and quaternary ammonium.

In one embodiment, $R^1$ is independently selected from the group consisting of methyl, ethyl, propyl, isopropyl, n-butyl, sec-butyl, tert-butyl, pentyl, hexyl and phenyl. In another embodiment, $R^2$ is independently selected from the group consisting of methyl, ethyl, propyl, isopropyl, butyl, hexyl and phenyl. In some embodiments, M is selected from the group consisting of Al, Zn, Ca, Ba, Mg, ammonium, melamine, melem, alkyl ammonium, and alkyl imidazole.

In one embodiment, $R_1$ is independently methyl or phenyl. In one embodiment, $R^2$ is independently methyl or ethyl. In some of these embodiments, n is 3. In some embodiments, M is a metal. In certain embodiments, M is aluminum and n is 3.

Other embodiments relate to compositions comprising carboxyethyl phosphinate esters and polymeric resin. In some embodiments, a composition comprises a salt of a carboxyethyl phosphinate ester. In one embodiment, the composition comprises a polymeric resin and a compound represented by Formula (I) as described herein.

In some of the foregoing embodiments, the composition comprises about 0.1 to about 50 parts by weight of the compound represented by Formula (I), based on about 100 parts by weight of the polymeric resin.

In some embodiments, the polymeric resin comprises one or more thermoplastic resins. For example, the one or more thermoplastic resins may be one or more of polystyrene resin (PS resin), acrylonitrile-butadiene-styrene terpolymer resin (ABS resin), rubber-modified high impact polystyrene resin (HIPS), acrylonitrile-styrene-acrylate terpolymer resin (ASA resin), acrylonitrile-styrene copolymer resin (SAN resin), methylmethacrylate-butadiene-styrene terpolymer resin (MBS resin), acrylonitrile-ethylacrylate-styrene terpolymer resin (AES resin), polycarbonate resin (PC resin), polyphenylene ether resin (PPE resin), polyethylene resin (PE resin), polypropylene resin (PP resin), polyethylene terephthalate (PET), polybutylene terephthalate (PBT), polymethyl methacrylate (PMMA), polyamide (PA) resin, copolymers thereof, and alloys thereof In one embodiment, the polymeric resin is polybutylene terephthalate. In another embodiment, the polymeric resin is a blend of the polyphenylene ether resin and the high impact polystyrene resin. In the foregoing embodiment, the polyphenylene ether resin is poly(2,6-dimethyl-1,4-phenylene ether).

Such compositions may further comprise one or more phosphate ester compounds. In some embodiments, the composition comprises about 0.1 to about 40 parts by weight of the phosphate ester, based on 100 parts by weight of the polymeric resin. In a particular embodiment, the phosphate ester is represented by the following Formula (II):

In the formula, each R is independently hydrogen or $C_{1-4}$ alkyl, X is derived from an aryl compound comprising at least two hydroxy groups, and n is 0 to 4. In some embodiments, the aryl compound comprising at least two hydroxy groups is selected from the group consisting of resorcinol, hydroquinone, bisphenol-A, and combinations thereof.

In one embodiment, the composition may be formed as a shaped article. In another embodiment, an article comprises one or more compositions as herein described. In a particular embodiment, a molded article comprises one or more compositions as herein described.

In some embodiments, the compositions as herein described have improved physical, mechanical and/or chemical properties. In some particular embodiments, the compositions have one or more of enhanced flame retardancy, color heat stability, and hygroscopicity.

In one embodiment, the composition has flame retardancy of at least V-1, when a specimen of the composition is tested according to the standard UL-94 VB. In another embodiment, the composition has flame retardancy of V-0, when a specimen of the composition is tested according to the standard UL-94 VB.

In one embodiment, the composition has ΔE of less than or equal to about 0.5, when a specimen of the composition measuring 5 cm×20 cm×0.32 cm is exposed to 270° C. for 10 minutes. In another embodiment, the composition has ΔE of less than or equal to about 0.3, when the specimen of the composition measuring 5 cm×20 cm×0.32 cm is exposed to 270° C. for 10 minutes.

In one embodiment, the composition has hygroscopicity of less than or equal to about 0.4%, when a specimen of the composition measuring 10 cm×10 cm×0.32 cm is allowed to stand in a thermostatic bath at 60° C. for 24 hours. In another embodiment, the composition has hygroscopicity of less than or equal to about 0.3%, when a specimen of the composition measuring 10 cm×10 cm×0.32 cm is allowed to stand in a thermostatic bath at 60° C. for 24 hours.

Also described herein are electronic devices comprising the compositions as described herein. In one embodiment, a method of making a plastic structure comprises providing the composition which includes the salt of the carboxyethyl phosphinate ester; and molding such composition into a shape. In another embodiment, a method of making an electronic device comprises providing an electronic circuit and providing a housing substantially enclosing the electronic circuit. Such housing may comprise a portion, which comprises the compositions as described herein.

DETAILED DESCRIPTION OF EMBODIMENTS

As noted above, one aspect of the invention is a carboxyethyl phosphinate ester compound. According to various embodiments, a salt of a carboxyethyl phosphinate ester is described. According to other embodiments, compositions comprising one or more salts of a carboxyethyl phosphinate ester are described. In some particular embodiments, compositions comprising one or more polymeric resins and one or more salts of a carboxyethyl phosphinate ester are described.

In various embodiments, salts of a carboxyethyl phosphinate esters are represented by Formula (I):

In the formula, $R^1$ is independently selected from $C_1$-$C_6$ alkyl, $C_6$-$C_{20}$ aryl, or $C_6$-$C_{20}$ alkyl substituted aryl, $R^2$ is independently selected from $C_1$-$C_6$ alkyl, $C_6$-$C_{30}$ aryl, or $C_6$-$C_{30}$ alkyl-substituted aryl, n is 1, 2, 3 or 4, and M is a metal or an amine. The compound according to Formula (I) is further described herein.

As indicated above, some embodiments include compositions comprising polymeric resins and the compound according to Formula (I). In some of these embodiments, the polymeric resin is a thermoplastic resin. Such compositions are further described herein. One advantage of some of these embodiments is one or more improved characteristics of the compositions selected from flame retardancy, color heat stability, and hygroscopicity, when compared to compositions comprising the same polymeric resins and other flame retardant materials such as aromatic phosphoric acid ester compounds. Such compositions of the embodiments may also maintain a good balance of other physical and mechanical properties. Another advantage of certain embodiments is the lack of a halogenated flame retardant compound.

Carboxyethyl Phosphinate Esters and Salts Thereof

In some embodiments, the composition contains a carboxyethyl phosphinate ester compound as described herein. In an embodiment, a compositions may comprise a salt of a carboxyethyl phosphinate ester. In certain embodiments, a salt of a carboxyethyl phosphinate ester compounds may be represented by Formula (I) below:

In the formula, $R^1$ is independently selected from $C_1$-$C_6$ alkyl, $C_6$-$C_{20}$ aryl, or alkyl substituted $C_6$-$C_{20}$ aryl, $R^2$ is independently selected from $C_1$-$C_6$ alkyl, $C_6$-$C_{30}$ aryl, or alkyl-substituted $C_6$-$C_{30}$ aryl, n is 1, 2, 3 or 4, and M is a metal or a charged amine.

In some embodiments, $R^1$ is independently selected from the group consisting of methyl, ethyl, propyl, isopropyl, n-butyl, sec-butyl, tert-butyl, pentyl, or hexyl. In some embodiments, $R^1$ may be an aryl substituted version of the foregoing alkyl groups. In some embodiments, $R^1$ is independently selected from phenyl, benzyl, napthyl, or anthracenyl, or alkyl substituted versions of the foregoing. In some embodiments, $R^1$ may be 1H-phenalenyl or pyrenyl. In some embodiments, $R^1$ includes alkyl combinations of the foregoing.

In some embodiments, $R^2$ is independently selected from the group consisting of methyl, ethyl, propyl, isopropyl, n-butyl, sec-butyl, tert-butyl, pentyl, or hexyl. In some embodiments, $R^1$ may be an aryl substituted version of the foregoing alkyl groups. In some embodiments, $R^1$ is independently selected from phenyl, benzyl, napthyl, or anthracenyl, or alkyl substituted versions of the foregoing. In some embodiments, $R^2$ may be 1H-phenalenyl or pyrenyl. In some embodiments, $R^2$ includes alkyl substituted combinations of the foregoing.

$R^1$ or $R^2$ may in some embodiments be an alkyl substituted aryl. While this alkyl substitution is a broad term and is to be construed in accordance with its ordinary meaning, and includes methyl, ethyl, propyl, isopropyl, n-butyl, sec-butyl, tert-butyl, pentyl, hexyl, heptyl, octyl, nonyl, among other alkyl substitutions on the aryl group.

The cation of the carboxyethyl phosphinate ester anion may be any ion. As such, the cation may have a positive charge of 1, 2, 3, 4, 5 and so forth. In some embodiments, the carboxyethyl phosphinate ester anionic molecules are equal in number to the charge of the cation. As is indicated in the formula, the cation may be a metallic ion or a charged amine. According to some embodiments, the amine is an ammonium moiety, and includes ammonium, primary ammonium moieties, second ammonium moieties, tertiary ammonium moieties, or quaternary ammonium moiety. In some particular embodiments, M is a metal. The metal may be any metal and includes such metals as Al, Zn, Ca, Ba or Mg. In some embodiment, M is selected from ammonium, melamine, melem, alkyl ammonium, and alkyl imidazole. In some embodiments, the imidazole is an N-alkyl substituted imidazole or is substituted at a carbon position on the imidazole.

As stated above, in some embodiments, a composition comprises both the salt of the carboxyethyl phosphinate ester and a polymeric resin. In some embodiments, the composition comprises about 0.1 to about 50 parts by weight of one or more salts of one or more carboxyethyl phosphinate esters, which includes, for example, approximately 1, 5, 10, 15, 20, 25, 30, 35, 40, 45 or 50 parts by weight. In certain embodiments, the composition may contain the one or more salts in an amount within a range formed by the two of the foregoing approximate parts by weigh. In other embodiments, the composition comprising the salt and the polymeric resin comprises about 50 to about 90 parts by weight of the salt. Here, the unit "parts by weight" refers to the weight of the one or more salts given that the total weight of the one or more polymeric resins is 100 parts by weight.

Polymeric Resins

As described above, some embodiments may additionally comprise a polymer resin. In some embodiments, the polymeric resin comprises one or more thermoplastic resins. Embodiments may also include thermosetting resins.

Examples of preferred polymeric resins include, but are not limited to, one or more of polystyrene resin (PS resin), acrylonitrile-butadiene-styrene terpolymer resin (ABS resin), high impact polystyrene resin (HIPS), acrylonitrile-styrene-acrylate terpolymer resin (ASA resin), acrylonitrile-styrene copolymer resin (SAN resin), methylmethacrylate-butadiene-styrene terpolymer resin (MBS resin), acrylonitrile-ethylacrylate-styrene terpolymer resin (AES resin), polycarbonate resin (PC resin), polyphenylene ether resin (PPE resin), polyethylene resin (PE resin), polypropylene resin (PP resin), polyethylene terephthalate (PET), polybutylene terephthalate (PBT), polymethyl methacrylate (PMMA), polyamide (PA) resin, copolymers thereof, or alloys thereof.

In some embodiments, the polymeric resin is one or more selected from the group consisting of polycarbonate resins, polyphenylene ether resins, styrene polymers, rubber modified acrylonitrile-styrene copolymers, copolymers thereof, and alloys thereof In some embodiments, the polymer resin is polybutylene terephthalate.

In some embodiments, the polymer resin is a blend of two more polymeric resins. In one embodiment, the polymer resin includes a blend of a polyphenylene ether resin and the high impact polystyrene resin. In one embodiment, the polyphenylene ether resin is poly(2,6-dimethyl-1,4-phenylene ether).

As stated above, in some embodiments, a composition comprises both the salt of the carboxyethyl phosphinate ester and a polymeric resin. In some embodiments, the composition comprises about 100 parts by weight of the one or more polymeric resins. As such, the 100 parts by weight of the one or more polymeric resins is used as the base "parts by weight" for the other components in the composition.

Other Flame Retardant Compounds

In some embodiments, the composition may further comprise additional available flame retardants compounds or flame retardant aids. In some embodiments, the compositions comprise one or more selected from organic phosphoric acid ester compounds, cyanurate compounds, metal salts, and fluorinated polyolefins. Such flame retardant compounds or aids may be used together with the salt of the carboxyethyl phosphinate ester.

In one embodiment, the composition comprises a polymer resin, a salt of a carboxyethyl phosphinate ester compound, and phosphate ester. In some embodiments, the composition comprises about 0.1 to about 40 parts by weight of the phosphate ester, based on the one or more polymer resins totaling 100 parts by weight.

In some embodiments, the polymer composition comprises an aromatic phosphate ester compound comprising the following structural Formula (II):

In formula (II), R on each phenyl group are each independently hydrogen, alkyl, or substituted alkyl, and are independent of an R on a different phenyl group. For example, R can be selected from methyl, ethyl, propyl, isopropyl, butyl, sec-butyl, tert-butyl. In some embodiments, R is selected from independent alkyl groups which comprise from two to four carbon atoms. However, embodiments are not limited to four carbon chains and may be branched alkyl groups. R may be selected independent from another R on the same or a different phenyl group of the aromatic phosphonate ester compound.

In formula (II), X is derived from an aryl compound comprising one or more hydroxy groups. In the formula, n is 0 to 4, including 0, 1, 2, 3 or 4.

For example, if X is derived from hydroquinone, then X would be a phenylene wherein a phenyl group would be disposed between the two oxygen atoms shown in the structural formula (as connected to X), and these oxygen atoms would be covalently bonded to the phenylene group in respective para positions. For another example, if X is derived from resorcinol, then X would be a phenylene wherein a phenyl group would be disposed between the two oxygen atoms shown in the structural formula (as connected to X), and these oxygen atoms would be covalently bonded to the phenylene group in respective meta positions. Other variations of this will be apparent to those having ordinary skill in the art. Thus, X can be derived from compounds such as hydroquinone, resorcinol, bisphenol A, naphthalene-2,6-diol, naphthalene-2,7-diol, and so forth. Thus, in some embodiments, X is arylene or multiple aryl groups.

Where n is 0, the aromatic phosphate ester compound may be triphenyl phosphate, tricresyl phosphate, trixylenyl phosphate, tri(2,6-dimethyl phenyl)phosphate, tri(2,4,6-trimethyl phenyl)phosphate, tri(2,4-ditertiary butyl phenyl)phosphate, tri(2,6-ditertiary butyl phenyl)phosphate, and the like; where n is 1, the aromatic phosphate ester compound may include resorcinol bis(diphenyl)phosphate, resorcinol bis(2,6-dimethyl phenyl)phosphate, resorcinol bis(2,4-ditertiary butyl phenyl)phosphate, hydroquinone bis(2,6-dimethyl phenyl) phosphate, hydroquinone bis(2,4-ditertiary butyl phenyl) phosphate, and the like. The aromatic phosphate ester compound can be used alone or in combination with other aromatic phosphate ester compounds.

In some embodiments, the composition may additionally comprise a flame retardant aid. Such aids may include, but are not limited to, metal salts, and anti-dropping agents including fluorinated polyolefin resins. Examples of suitable metal salts include widely known metal sulfonates. Examples of anti-dripping agents include, but are not limited to, resins such as polytetrafluoroethylene, polyvinylidene fluoride, tetrafluoroethylene/vinylidene fluoride copolymer, tetrafluoroethylene/hexafluoropropylene copolymer and ethylene/tetrafluoroethylene copolymer. In some embodiments, the composition may comprise one or more flame retardant aids. According to some embodiments, the compositions may comprise about 0.1 to about 30 parts by weight of the one or more flame retardant aids, based on about 100 parts by weight of the polymeric resin.

Additional Components

According to embodiments, the composition may contain one or more compounds or polymers in addition to the foregoing components. Additional components or additives may be added to provide additional properties or characteristics to the composition or to modify existing properties of the composition. Other additives that may be contained in the composition include, but are not limited to an impact modifier, a plasticizer, inorganic filler, a heat stabilizer, an anti-oxidant, a compatibilizer, a light stabilizer, a reinforcing agent, a lubricant, a pigment, and/or dye. The additives are employed in the amount of about 0 to about 60 parts by weight on the basis of 100 parts by weight of the one or more polymer resins. For example, an inorganic filler such as glass fiber, carbon fiber, talc, silica, mica, and alumina may be added to improve mechanical strength and heat distortion temperature of the resin composition. One of ordinary skill in the art will appreciate that various additives may be added to the compositions according to embodiments of the invention.

Preparation of Embodiments of Compositions Comprising Polymer Resins

In some embodiments, the compositions comprising the salt and the polymeric resin are prepared by mixing their components. In some embodiments, one or more other additives may be mixed together with the components of the composition. In some embodiments, one or more component resins may be heated to melt prior to the mixing or the composition may be heated during the mixing. The mixing may occur when each components is in a solid, liquid, or dissolved state, or mixtures thereof In one embodiment, the above components are mixed together all at once. Alternatively, one or more components are added individually. For example, the polymeric resin may first be mixed with the impact modifier, prior to mixing this admixture with the remaining components. Formulating and mixing the components may be made by any method known to those persons having ordinary skill in the art, or those methods that may be later discovered. The mixing may occur in a pre-mixing state in a device such as a ribbon blender, followed by further mixing in a Henschel mixer, Banbury mixer, a single screw extruder, a twin screw extruder, a multi screw extruder, or a cokneader.

Enhanced Properties

An advantage of certain preferred embodiments is that they provide compositions comprising polymeric resins which have one or more of good flame retardancy, color heat stability, and hygroscopicity. In some embodiments, the composition also have other physical and mechanical properties in combination with the one or more enhanced properties.

Certain embodiments of the compositions have excellent flame retardancy. In some embodiments, when samples of the compositions are tested under the standard UL94 VB (⅛"), the samples had a flame retardancy of at least V-1. In some embodiments, when samples of the compositions are tested under the standard UL94 VB (⅛"), the samples had a flame retardancy of V-0.

In some embodiments, the compositions exhibit good thermal stability of sample color when a specimen of the composition is exposed to high temperatures. In one embodiment, a composition comprising the salt of the carboxyethyl phosphinate ester and a polymer resin had $\Delta E$ of less than or equal to about 0.5 when a 5 cm×20 cm×0.32 cm sample was exposed to 270° C. for 10 minutes. In another embodiment, a composition comprising the salt of the carboxyethyl phosphinate ester and a polymer resin had $\Delta E$ of less than or equal to about 0.4 when a 5 cm×20 cm×0.32 cm sample was exposed to 270° C. for 10 minutes. In another embodiment, a composition comprising the salt of the carboxyethyl phosphinate ester and a polymer resin had $\Delta E$ of less than or equal to about 0.5 when a 5 cm×20 cm×0.32 cm sample was exposed to 270° C. for 10 minutes.

In some embodiments, the compositions exhibit enhanced hygroscopicity. In one embodiment, a composition comprising the salt of the carboxyethyl phosphinate ester and a polymer resin had hygroscopicity of less than or equal to about 0.4% when a specimen of the sample measuring 10 cm×10 cm×0.32 cm was allowed to exposed to water in a thermostatic bath at 60° C. for 24 hours. In another embodiment, a composition comprising the salt of the carboxyethyl phosphinate ester and a polymeric resin had hygroscopicity of less than or equal to about 0.3% when a specimen of the sample measuring 10 cm×10 cm×0.32 cm was allowed to exposed to water in a thermostatic bath at 60° C. for 24 hours. In another embodiment, a composition comprising the salt of the carboxyethyl phosphinate ester and a polymeric resin had hygroscopicity of less than or equal to about 0.2% when a specimen of the sample measuring 10 cm×10 cm×0.32 cm was allowed to exposed to water in a thermostatic bath at 60° C. for 24 hours.

Shaped Articles of Electronic Devices

Another embodiment provides a shaped article using the compositions comprising a polymer resin according to the foregoing embodiments. The compositions may be molded into various shapes. For molding with the composition, an extrusion molding machine such as a vented extruder may be used. The polymer composition of embodiments may be molded into various moldings using, for example, a melt-molding device. In embodiments, the polymer composition is formed into a pellet, which then may be molded into various shapes using, for example, injection molding, injection compression molding, extrusion molding, blow molding, pressing, vacuum forming or foaming. In one embodiment, the polymer composition can be made into a pellet using meltkneading, and the resulting pellets are molded into moldings through injection molding or injection compression molding.

As noted, in one embodiment, the compositions comprising a polymeric resin are formed into pellets. In other embodiments, the compositions are formed into structural parts of various consumer products, including electronic devices and appliances. In some embodiments, the compositions are molded into a housing or body of electronic or non-electronic devices. Examples of electrical devices in which a molded article made of the blend of the composition according to embodiments of the invention include printers, computers, word processors, keyboards, personal digital assistants (PDA), telephones, mobile phones, facsimile machines, copy machines, electronic cash registers (ECR), desk-top electronic calculators, PDAs, cards, stationery holders, washing machines, refrigerators, vacuum cleaners, microwave ovens, lighting equipment, irons, TV, VTR, DVD players, video cameras, radio cassette recorders, tape recorders, mini disc players, CD players, speakers, game machines, liquid crystal displays, MP3 players, and electric or electronic parts and telecommunication equipment, such as connectors, relays, condensers, switches, printed circuit boards materials, coil bobbins, semiconductor sealing materials, electric wires, cables, transformers, deflecting yokes, distribution boards, clocks, watches, and the like.

The features of the invention may be further described with reference to the following examples. These examples are intended for the purpose of illustration and are not to be construed any way as to limit the scope of the present invention.

EXAMPLES (A) Preparation of Salt Compounds of Carboxyethyl Phosphinate Esters

The salt of carboxyethyl phosphinate ester was obtained by reacting 2-methyl-1,2-oxaphosphinolan-5-one-2-oxide with alcohol to prepare carboxyethyl phosphinate ester, which was then deprotonated, resulting in the salt.

(A1) Aluminum Salt of Methyl Carboxyethyl Methylphosphinate Ester

Figure 1:
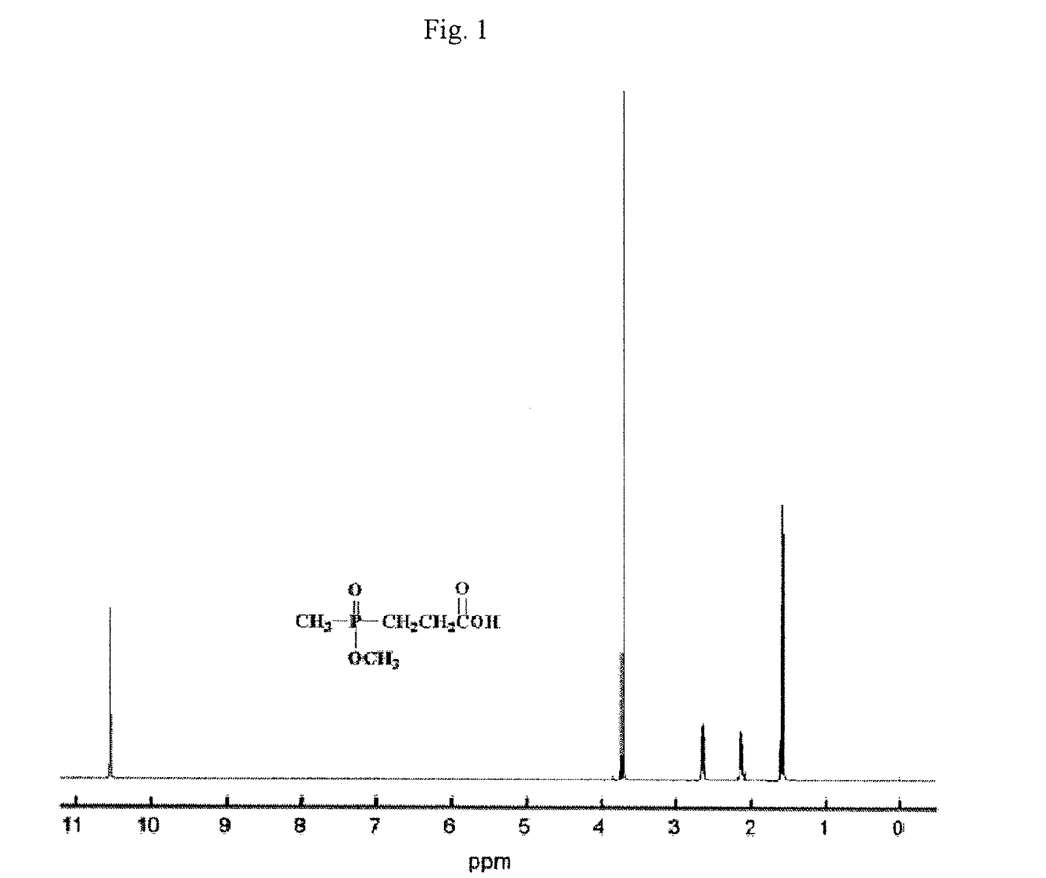
FIG. 1 is a $^1$H NMR spectrum of methyl carboxyethyl methylphosphinate.

Into a four-necked flask fitted with a thermometer, a condenser, a stirrer and a dropping funnel, dichloromethylphosphine (0.5 mol. 58.46 g) was added and then stirred at 80° C. for 1 hour in a nitrogen atmosphere while dropping excess acrylic acid in an amount of 1.2 times that required (0.6 mol. 43.24 g) thereon. The temperature was increased to 130° C. and the reaction mixture was further stirred for 2 hours. Subsequently, the temperature was decreased to 50° C., after which the reaction mixture was allowed to react for about 2 hours while dropping acetic anhydride (0.6 mol. 174.64 g) thereon. After the completion of the reaction, the resultant reaction solution was cooled to room temperature, precipitated using ether, and then vacuum filtered. The residual ether was removed in a vacuum oven. The resultant 2-methyl-1,2-oxaphosphinolan-5-one-2-oxide (0.5 mol. 67.04 g) was added along with methanol (0.6 mol. 19.22 g) into a flask and then refluxed at 50° C. for about 10 hours. After the completion of the reaction, the reaction solution was vacuum distilled, thus obtaining a product. The result of a $^1$H NMR analysis of the product is shown in FIG. 1.

Methyl carboxyethyl methylphosphinate (1 mol. 134.0 g) thus obtained and aluminum trihydroxide (0.33 mol. 35.0 g) were added to 500 ml of water, and the reaction mixture was stirred at 170° C. for 6 hours using a mechanical stirrer. After the completion of the reaction, the temperature was decreased to 50° C., and the precipitate was filtered and then washed with water. Subsequently, water was removed at 100° C. under reduced pressure, therefore obtaining an aluminum salt of methyl carboxyethyl methylphosphinate ester.

(A2) Aluminum Salt of Ethyl Carboxyethyl Methylphosphinate Ester

Figure 2:
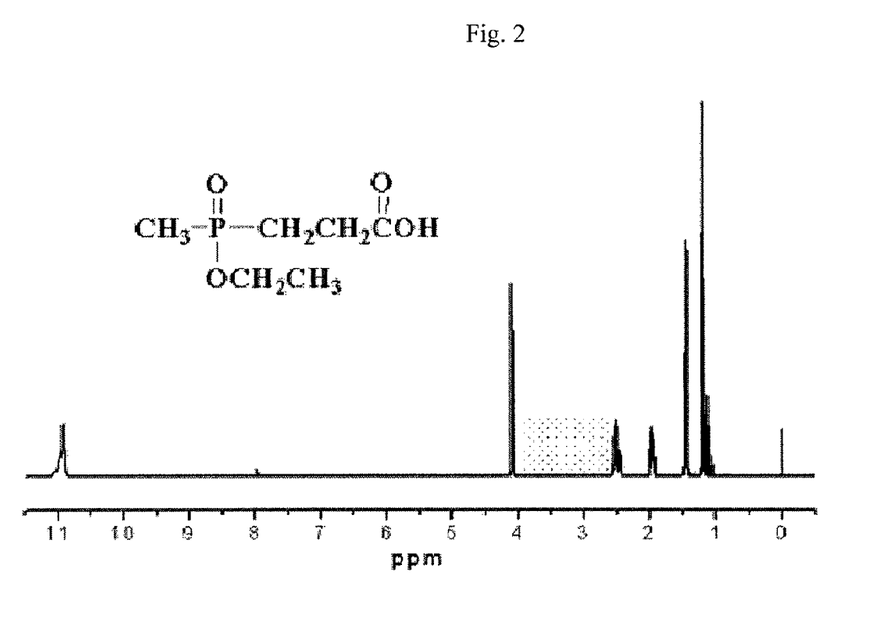
FIG. 2 is a $^1$H NMR spectrum of ethyl carboxyethyl methylphosphinate.

The aluminum salt of ethyl carboxyethyl methylphosphinate ester was prepared in the same manner as the aluminum salt of methyl carboxyethyl methylphosphinate ester in (A1), with the exception that 2-methyl-1,2-oxaphosphinolan-5-one-2-oxide was reacted with ethanol to prepare ethyl carboxyethyl methylphosphinate. The $^1$H NMR analysis of the resultant compound is shown in FIG. 2.

(A3) Aluminum Salt of Methyl Carboxyethyl Phenylphosphinate Ester

Figure 3:
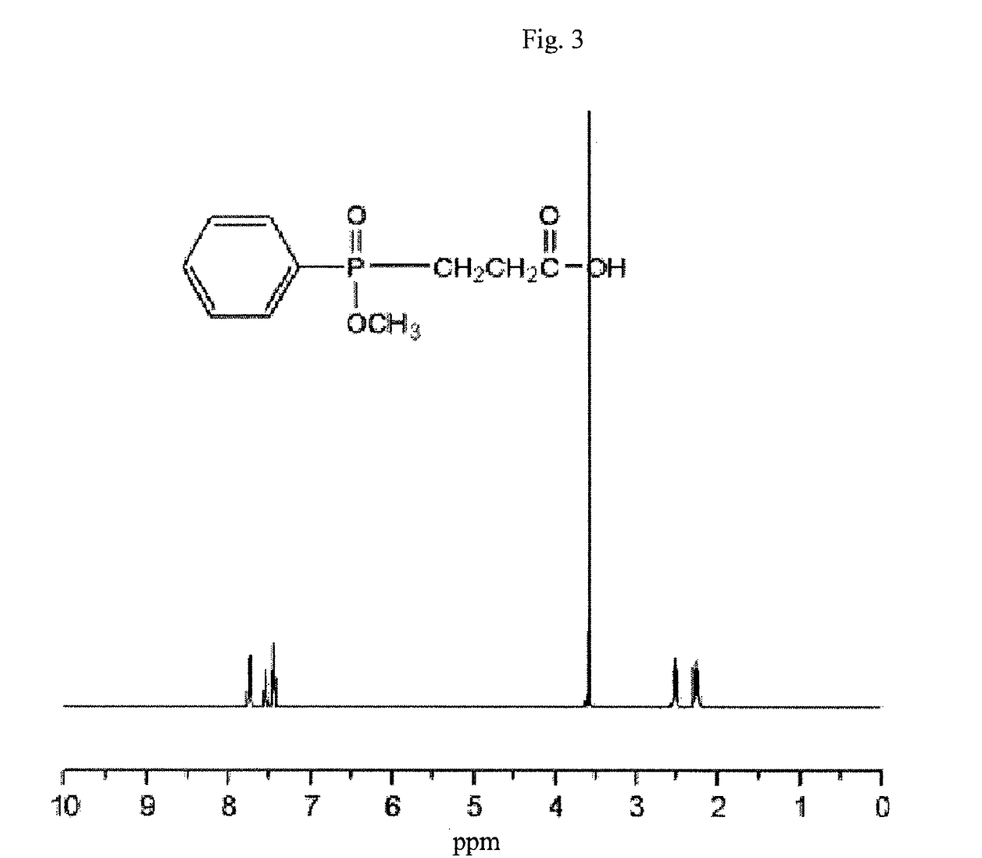
FIG. 3 is a $^1$H NMR spectrum of methyl carboxyethyl phenylphosphinate.

The title compound was prepared in the same manner as the aluminum salt of methyl carboxyethyl methylphosphinate ester in (A1), with the exception that 2-phenyl-1,2-oxaphosphinolan-5-one-2-oxide was reacted with methanol to prepare methyl carboxyethyl phenylphosphinate. The $^1$H NMR analysis of the resultant compound is shown in FIG. 3.

(B) Thermoplastic Resin (B1) Rubber Modified SAN Copolymer Resin (ABS Resin)

(B11) g-ABS Resin 50 parts by weight of solid butadiene rubber latex was added with 36 parts by weight of styrene and 14 parts by weight of acrylonitrile as grafting monomers and 150 parts by weight of deionized water. Subsequently, based on the total solid content, 1.0 part by weight of potassium oleate, 0.4 parts by weight of cumene hydroperoxide, 0.2 parts by weight of a mercaptan chain transfer agent, 0.4 parts by weight of glucose, 0.01 parts by weight of iron sulfate hydrate, and 0.3 parts by weight of sodium pyrophosphate were added, and then the reaction mixture was allowed to stand at 75° C. for 5 hours. After the completion of the reaction, graft latex was prepared, added with 0.4 parts by weight of sulfuric acid based on the solid content of the resin, and then solidified, thus preparing graft copolymer resin (g-ABS) powder.

(B12) SAN Copolymer Resin 75 parts by weight of styrene, 25 parts by weight of acrylonitrile, 120 parts by weight of deionized water, 0.15 parts by weight of azobisisobutyronitrile, 0.4 parts by weight of tricalcium phosphate, and 0.2 parts by weight of a mercaptan chain transfer agent were added. After the reaction temperature was increased from room temperature to 80° C. over 90 min, the reaction mixture was allowed to stand at the increased temperature for 180 min to prepare copolymer resin (SAN), which was then washed with water, dehydrated, and dried, thus preparing SAN powder.

The rubber modified SAN copolymer resin was obtained by mixing and compounding 30 parts by weight of (B11) g-ABS resin and 70 parts by weight of (B12) SAN copolymer resin.

(B2) High Impact Polystyrene Resin (HIPS Resin)

High impact polystyrene resin HG-1730, available from Cheil Industries Inc., Korea, was used, which had 7.5% rubber content and an average rubber particle size of 0.4 µm.

(B3) Polyphenylene Ether Resin (PPE Resin)

Poly(2,6-dimethyl-phenylether) (trade name: S-202), available from Asahi Kasehi Corp. (Japan) in the form of powder having an average particle size of tens of µm, was used.

(B4) Glass Fiber Reinforced Polybutylene Terephthalte Resin (Glass Reinforced PBT Resin)

70 wt % of polybutylene terephthalate resin (trade name: Tribit 1500), available from Samyang Corp. (Korea), was reinforced with 30 wt % of glass fiber and then used.

(C) Carboxy Phosphinic Acid Compound

2-Carboxyethyl methylphosphinate was used.

(D) Organic Phosphoric Acid Ester

Bisphenol-A diphenyl phosphate (trade name: CR-741, available from Daihachi Chem. Co., Ltd.) was used.

Examples 1-9 and Comparative Examples 1-6

Each of the compositions of Examples 1-9 and Comparative Examples 1-6 was prepared according to the composition ratios shown in Tables 1 and 2 below using the above components. As such, individual components were extruded at 200-280° C. using a twin screw extruder to prepare pellets, which were then dried at 80° C. for 2 hours and thereafter injection molded under conditions of a molding temperature of 180-280° C. and a mold temperature of 40-80° C. using a 6 Oz injection molding machine, thus manufacturing a sample. The properties of each sample were evaluated. The results are given in Tables 1 and 2 below.

TABLE 1

| | | Examples | | | | | | | | |
|---|---|---|---|---|---|---|---|---|---|---|
| | | 1 | 2 | 3 | 4 | 5 | 6 | 7 | 8 | 9 |
| (A) | (A1) | 40 | — | — | 20 | — | 20 | 30 | 10 | 15 |
| | (A2) | — | 40 | — | — | 20 | — | — | — | — |
| | (A3) | — | — | 40 | — | — | — | — | — | — |
| (B) | (B11) | 30 | 30 | 30 | — | — | — | 30 | — | — |
| | (B12) | 70 | 70 | 70 | — | — | — | 70 | — | — |
| | (B2) | — | — | — | 60 | 60 | — | — | 60 | — |
| | (B3) | — | — | — | 40 | 40 | — | — | 40 | — |
| | (B4) | — | — | — | — | — | 100 | — | — | 100 |
| (C) | | — | — | — | — | — | — | — | — | — |
| (D) | | — | — | — | — | — | — | 10 | 10 | 5 |
| UL94 Flame Retardancy (1/8") | | V-1 | V-1 | V-1 | V-0 | V-0 | V-0 | V-1 | V-0 | V-0 |
| Color Heat Stability (ΔE) | | 0.5 | 0.4 | 0.4 | 0.3 | 0.3 | 0.4 | 0.3 | 0.2 | 0.2 |
| Hygroscopicity (%) | | 0.4 | 0.4 | 0.3 | 0.2 | 0.3 | 0.4 | 0.3 | 0.4 | 0.3 |

TABLE 2

| | | Comparative Examples | | | | | |
|---|---|---|---|---|---|---|---|
| | | 1 | 2 | 3 | 4 | 5 | 6 |
| (A) | (A1) | — | — | — | — | — | — |
| | (A2) | — | — | — | — | — | — |
| | (A3) | — | — | — | — | — | — |
| (B) | (B11) | 30 | — | — | 30 | — | — |
| | (B12) | 70 | — | — | 70 | — | — |
| | (B2) | — | 60 | — | — | 60 | — |
| | (B3) | — | 40 | — | — | 40 | — |
| | (B4) | — | — | 100 | — | — | 100 |
| (C) | | 40 | 20 | 20 | 30 | 10 | 15 |
| (D) | | — | — | — | 10 | 10 | 5 |
| UL94 Flame Retardancy (1/8") | | Fail | V-0 | V-1 | Fail | V-0 | Fail |
| Color Heat Stability (ΔE) | | 1.8 | 1.0 | 1.2 | 1.5 | 1.1 | 1.1 |
| Hygroscopicity (%) | | 2.5 | 1.9 | 2.4 | 2.3 | 1.4 | 2.0 |

Evaluation of Properties (1) UL 94 VB Flame Retardancy

The sample was produced to a thickness of ⅛" and measured for flame retardancy according to the UL 94 VB method.

(2) Color Heat Stability (ΔE)

The sample was injection molded into a 5 cm×20 cm×0.32 cm sample at a molding temperature of 270° C. for a residence time of 10 min using a pinpoint gate mold of a 6 oz injection molding machine. The sample was observed before and after the residence time using a Minolta spectrophotometer, and thus color heat stability was judged.

(3) Hygroscopicity (%)

A 10 cm×10 cm×0.32 cm injected sample was allowed to stand in a thermostatic bath at 60° C. for 24 hours. The difference in weight before and after the sample was allowed to stand was measured and thus hygroscopicity was determined.

From the results of Tables 1 and 2, it can be confirmed compositions comprising the salt of carboxyethyl phosphinate ester and a polymeric resin have excellent flame retardancy, color heat stability and hygroscopicity. Such compositions represent certain advantages over compositions which do not comprise the salt of the carboxyethyl phosphinate ester.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the invention has been disclosed in the context of certain embodiments and examples, it will be understood by those skilled in the art that the invention extends beyond the specifically disclosed embodiments to other alternative embodiments and/or uses and obvious modifications and equivalents thereof Accordingly, the invention is not intended to be limited by the specific disclosures of embodiments herein.

What is claimed is:

1. A compound represented by Formula (I):

wherein $R^1$ is independently selected from the group consisting of $C_1$-$C_6$ alkyl, $C_6$-$C_{20}$ aryl group and alkyl-substituted $C_6$-$C_{20}$ aryl, wherein $R^2$ is independently selected from the group consisting of $C_1$-$C_6$ alkyl, $C_6$-$C_{30}$ aryl, and alkyl-substituted $C_6$-$C_{30}$ aryl group, wherein n is 1, 2, 3 or 4, and wherein M is selected from the group consisting of Al, melem and alkyl imidazole.

2. The compound of claim 1, wherein $R^1$ is independently selected from the group consisting of methyl, ethyl, propyl, isopropyl, n-butyl, sec-butyl, tert-butyl, pentyl, hexyl and phenyl.

3. The compound of claim 1, wherein $R^2$ is independently selected from the group consisting of methyl, ethyl, propyl, isopropyl, butyl, hexyl and phenyl.

4. A composition comprising:
   a polymeric resin; and
   the compound of claim 1.

5. The composition of claim 4, wherein the composition comprises about 0.1 to about 50 parts by weight of the compound represented by Formula (I), based on 100 parts by weight of the polymeric resin.

6. The composition of claim 4, wherein the polymeric resin comprises one or more from the group consisting of polystyrene resin (PS resin), acrylonitrile-butadiene-styrene terpolymer resin (ABS resin), rubber-modified high impact polystyrene resin (HIPS), acrylonitrile-styrene-acrylate terpolymer resin (ASA resin), acrylonitrile-styrene copolymer resin (SAN resin), methylmethacrylate-butadiene-styrene terpolymer resin (MBS resin), acrylonitrile-ethylacrylate-styrene terpolymer resin (AES resin), polycarbonate resin (PC resin), polyphenylene ether resin (PPE resin), polyethylene resin (PE resin), polypropylene resin (PP resin), polyethylene terephthalate (PET), polybutylene terephthalate (PBT), polymethyl methacrylate (PMMA), polyamide (PA) resin, and copolymers thereof.

7. The composition of claim 4, further comprising a phosphate ester.

8. The composition of claim 7, wherein the composition comprises about 0.1 to about 40 parts by weight of the phosphate ester, based on 100 parts by weight of the polymeric resin.

9. The composition of claim 7, wherein the phosphate ester comprises a compound represented by the following Formula (II):

wherein each R is independently hydrogen or $C_{1-4}$ alkyl;
X is derived from an aryl compound comprising at least two hydroxy groups;
and n is 0 to 4.

10. The composition of claim 9, wherein the aryl compound comprising at least two hydroxy groups is selected from the group consisting of resorcinol, hydroquinone, bisphenol-A, and combinations thereof.

11. The composition of claim 4, formed as a shaped article.

12. The composition of claim 4, wherein the composition has flame retardancy of at least V-1, when a specimen of the composition is tested according to the standard UL-94 VB.

13. The composition of claim 4, wherein the composition has flame retardancy of V-0, when a specimen of the composition is tested according to the standard UL-94 VB.

14. The composition of claim 4, wherein the composition has ΔE of less than or equal to about 0.5, when a specimen of the composition measuring 5 cm×20 cm×0.32 cm is exposed to 270° C. for 10 minutes.

15. The composition of claim 4, wherein the composition has ΔE of less than or equal to about 0.3, when the specimen of the composition measuring 5 cm×20 cm×0.32 cm is exposed to 270° C. for 10 minutes.

16. The composition of claim 4, wherein the composition has hygroscopicity of less than or equal to about 0.4%, when a specimen of the composition measuring 10 cm×10 cm×0.32 cm is allowed to stand in a thermostatic bath at 60° C. for 24 hours.

17. The composition of claim 4, wherein the composition has hygroscopicity of less than or equal to about 0.3%, when a specimen of the composition measuring 10 cm×10 cm×0.32 cm is allowed to stand in a thermostatic bath at 60° C. for 24 hours.

18. An electronic device comprising the composition of claim 4.

19. A method of making a plastic structure comprising molding the composition of claim 4 into a molded structure.

* * * * *